United States Patent [19]

Inomata et al.

[11] Patent Number: 5,736,107
[45] Date of Patent: Apr. 7, 1998

[54] APPARATUS FOR OXIDATIVE COUPLING OF METHANE

[75] Inventors: Makoto Inomata; Tsutomu Katagiri, both of Yokohama; Kozo Imura, Handa; Erli Sun, Yokohama, all of Japan

[73] Assignees: Japan National Oil Corporation; Sekiyushigen Kaihatsu Kabushiki Kaisha; Cosmo Research Institute, all of Tokyo, Japan

[21] Appl. No.: 787,046

[22] Filed: Jan. 28, 1997

Related U.S. Application Data

[62] Division of Ser. No. 564,556, Nov. 21, 1995.

[30]     Foreign Application Priority Data

Dec. 5, 1994  [JP]  Japan ................................. 6-301216

[51] Int. Cl.⁶ ................................................. F27B 15/08
[52] U.S. Cl. ............................ 422/144; 422/145; 422/147; 422/198; 422/213
[58] Field of Search ................................. 422/144, 145, 422/147, 198, 213; 585/312, 313, 324, 500, 943

[56]     References Cited

U.S. PATENT DOCUMENTS

| | | | |
|---|---|---|---|
| 4,789,458 | 12/1988 | Haddad et al. | 208/151 |
| 4,963,328 | 10/1990 | Haddad et al. | 422/144 |
| 5,080,872 | 1/1992 | Jezl et al. | 422/201 |
| 5,248,408 | 9/1993 | Owen | 208/113 |
| 5,288,920 | 2/1994 | Chan et al. | 422/146 |
| 5,599,510 | 2/1997 | Kaminsky et al. | 422/197 |

FOREIGN PATENT DOCUMENTS

WO 91/12224  8/1991  WIPO.

*Primary Examiner*—Nina Bhat
*Attorney, Agent, or Firm*—Oblon, Spivak, McClelland, Maier & Neustadt, P.C.

[57]     ABSTRACT

An apparatus for oxidative coupling of methane having a coupling reactor in the shape of a vertical pipe, a gas-solid separator, a catalyst feedback system and, between the gas-solid separator and catalyst feedback system, a catalyst cooling system for cooling the catalyst.

4 Claims, 4 Drawing Sheets

APPARATUS FOR OXIDATIVE COUPLING OF METHANE

This is a Division of application Ser. No. 08/564,556 filed on Nov. 21, 1995, pending.

BACKGROUND OF THE INVENTION

1. Field of the Invention

The present invention relates to a method for producing a hydrocarbon having a carbon number of at least 2, such as ethylene, by means of oxidative coupling of methane, and to an apparatus to be used in the method. In particular, the present invention relates to a method for oxidative coupling of methane, at an excellent conversion and thermal efficiency, which employs a relatively small-scale and simple apparatus for producing a hydrocarbon having a carbon number of at least 2 such as ethylene, which is useful as liquid fuel and material for various organic syntheses, from a methane source such as natural gas, as well as relating to such an apparatus.

2. Background Art

In recent years, demand for natural gas as an energy resource or a material for chemical syntheses has been increasing. This is considered to be due to the greater deposited amount of natural gas than that of petroleum, exhaustion of which is foreseen, and due to the small discharge amount of carbon dioxide gas from natural gas combustion per its calorific value, giving it a relatively small influence on global warming. In recent years, exploration activities have achieved many discoveries of natural gas deposits; however, there are many cases in which these discoveries have not proceeded to exploitation since exploitation according to conventional techniques requires a large amount of plant and equipment investment, and since the infrastructure, such as pipelines, at the discovery areas are insufficient. Techniques for liquefaction of natural gas have been put to practical use, such as a technique of producing liquefied natural gas (LNG) at an extremely low temperature under a high pressure, and a technique of converting natural gas into liquid hydrocarbon fuel via production of synthesis gas according to steam reforming; however, important problems in proceeding to exploitation of a gas field exist in the large amounts of exploitation investment, such as plant and equipment investment and operating costs, according to any of these conventional techniques. Therefore, in order to make effective use of natural gas which is discovered in a remote area, establishment of a technique for converting natural gas into liquid hydrocarbon fuel, which is more efficient and requires less cost than conventional techniques, has been desired.

In order to make effective use of methane, a technique has been sought after for converting the entire amount of natural gas containing methane into liquid fuel or synthesis raw material, which has a boiling point higher than that of the natural gas, by means of a simple installation and method which can be employed at the place of natural gas production.

Methods for producing liquid fuel from natural gas have been hitherto known such as an indirect method in which natural gas is converted into a synthesis gas which contains $H_2$ and CO by a process such as steam reforming, and then liquid fuel such as methanol, gasoline, kerosene, gas oil or the like is produced by another process such as the Fischer-Tropsch process; as well as a direct method in which methane, which is a main component of natural gas, is converted by a methane oxidative coupling reaction into unsaturated lower hydrocarbons such as ethylene, and then liquid fuel or the like is produced by a polymerization reaction. Among these methods, interest has been focused on direct methods in recent years since an indirect method requires a large-scale apparatus in the process of producing the synthesis gas, and, in addition, since indirect methods have complicated procedures due to incorporation of processes such as the Fischer-Tropsch synthetic process.

Methane oxidative coupling (hereinafter simply referred to as "coupling") reaction is a reaction in which methane is allowed to react with oxygen in the presence of a catalyst at a temperature of at least 500° C. so as to produce unsaturated lower hydrocarbons (mainly ethylene), saturated lower hydrocarbons (mainly ethane), water, and the like, as represented by the following formula (1):

$$CH_4, O_2 \rightarrow C_2H_6, C_2H_4, H_2O \tag{1}$$

Since a combustion reaction of methane also proceeds along with the above reaction in this temperature range, a part of the methane is consumed in this combustion reaction so as to produce carbon oxides, such as carbon oxide (CO) and carbon dioxide ($CO_2$), as by-products. In addition, since the coupling reaction and the combustion reaction are exothermic reactions which generate a large amount of heat, the temperature in the system of the reaction abruptly rises. In a methane coupling reaction in general, the reaction does not progress sufficiently at a temperature lower than 500° C., at which the activity of the catalyst is low; and the yield of product hydrocarbons decreases at a temperature exceeding 900° C., at which the combustion reaction becomes dominant. Therefore, the key is to establish an economical direct method to make effective use of the generated heat and the by-product carbon dioxides while maintaining the reaction temperature between 500° C. and 900° C.

A coupling process which has been conducted in a conventional fixed-bed adiabatic reactor is not practical since the ratio of conversion into unsaturated hydrocarbons with a temperature increase in the range between 350° C. and 400° C., which is the range within which the temperature is permitted to increase, is between 10% and 15% at highest. A fluidized-bed reactor, which improves efficiency in heat exchange, is operable at a higher methane conversion; however, a process using such a fluidized-bed reactor requires great cost for installing a large-scale cooling system such as a huge cooling pipe, so as to remove a lot of the reaction heat. Furthermore, such a reactor alone cannot make effective use of the generated heat and the by-product carbon oxides.

Methods which can solve the above problems have been proposed such as a method in which saturated hydrocarbons of carbon numbers of at least 2 are introduced into a coupling reactor together with methane, and then the saturated hydrocarbons are pyrolyzed using the large amount of heat generated in the methane oxidative coupling so as to obtain unsaturated hydrocarbons and hydrogen. Moreover, there is a publication concerning a trial in which the hydrogen produced in the above reaction is allowed to react in a methanation reactor with the carbon oxides which are produced as by-products in the system, so as to produce methane, which is fed back to the coupling reactor (see J. H. Edwards, K. T. Do, R. J. Tyler, 1989 International Chemical Congress of Pacific Basin Societies, Honolulu, Dec. 17–22, No. 169).

Although these methods which have hitherto been proposed gave some suggestions for efficient use of the large amount of generated heat and the by-product carbon oxides, problems still remain. For example, in the case where a methane oxidative coupling and a pyrolysis of saturated hydrocarbons are carried out in the same reactor, it is extremely difficult to control the temperature since the former reaction is exothermic while the latter is endothermic. In addition, a method for controlling the reaction temperature in this process has not yet been suggested. Furthermore, with respect to the molar ratios of the carbon oxides and $H_2$ which are produced in this reaction, the amount of the carbon oxides is excessive for methanation in the methanation reactor; therefore, in order to regulate the molar ratios, a methanation which requires burdensome installation and energy must be carried out, in which, for example, the entire amount of $CO_2$ produced in the reaction system is once separated and removed in a decarbonation process, and then, to the residual gas which does not contain $CO_2$, $CO_2$ in a stoichiometric ratio for the methanation reaction is added.

SUMMARY OF THE INVENTION

The present invention intends to solve the above problems; therefore, the object of the present invention is to provide a methane oxidative coupling method and an apparatus therefor by which a hydrocarbon having a carbon number of at least 2 (hereinafter referred to as "$C_{2+}$") can be economically produced at a high yield by effectively controlling the temperature in the reaction system using a simple method as well as by making effective use of the generated reaction heat and the by-product carbon oxides.

The above object can be solved by providing a method for oxidative coupling of methane which is characterized by comprising: a coupling step, in which a coupling feed gas containing methane and a gas containing oxygen are supplied to a conveying catalyst bed which is formed by an ascending gas stream which contains a catalyst, and then methane and oxygen are allowed to react so as to produce a coupling product gas; a catalyst separation step for separating the catalyst from the coupling product gas; and a catalyst feedback step for feeding back the thus-separated catalyst to the coupling step.

According to the method for oxidative coupling of methane, since the coupling feed gas and the gas containing oxygen are supplied to the conveying catalyst bed which is formed by an ascending stream which contains a catalyst, the reaction system does not accumulate excessive heat, the combustion reaction as a side reaction is hindered, and the selectivity of the coupling reaction is enhanced. Furthermore, as the result of the reduction in the temperature of the fed-back catalyst and the smooth controllability of the temperature during the coupling reaction, the yield of the $C_{2+}$ hydrocarbon is improved.

DESCRIPTION OF THE PREFERRED EMBODIMENTS

Figure 1:
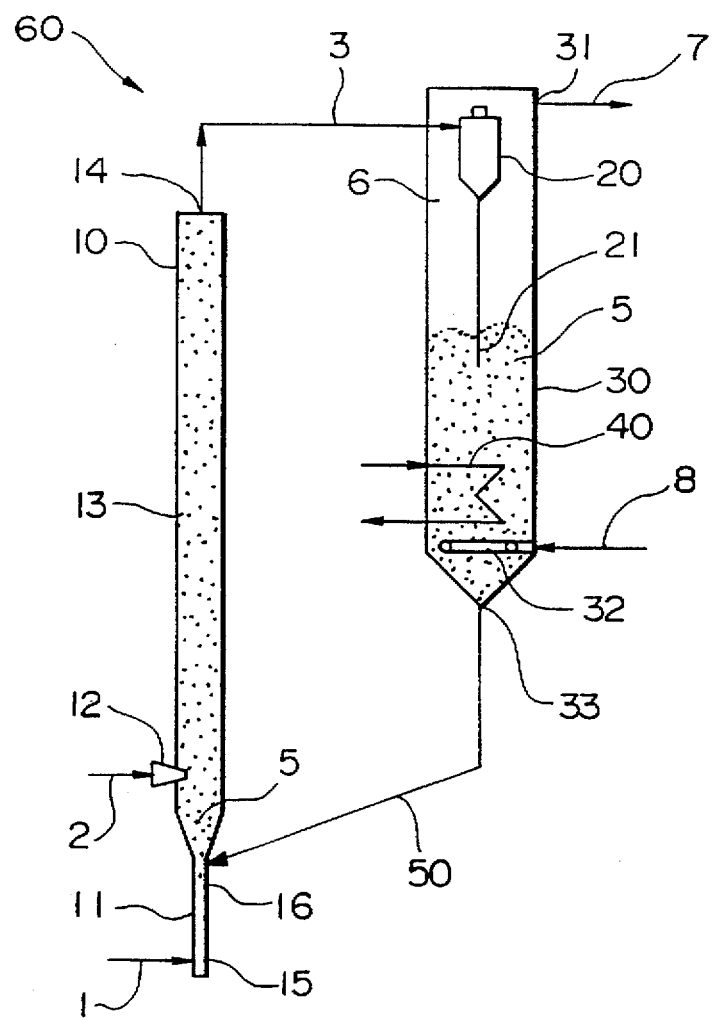
FIG. 1 is a cross-sectional view of an embodiment of the coupling apparatus according to the present invention.

The conveying catalyst bed used in the coupling method of the present invention can be formed in a manner such that catalyst particles are entrained by at least a part of the coupling feed gas. When this is the case, at least a part of the coupling feed gas can be supplied to an intermediate position of the conveying catalyst bed. The gas containing oxygen is supplied preferably to an intermediate position of the conveying catalyst bed.

The molar ratio of oxygen/methane which are supplied to the coupling step is preferably between 0.05 and 0.5. The amount of the catalyst which is supplied to the coupling step is preferably between 0.5% and 5% by volume with respect to the volume of the entirety of gas supplied to the coupling step in the conveying catalyst bed. The reaction temperature in the coupling step is maintained preferably between 750° C. and 900° C. The reaction pressure in the coupling step is maintained preferably between atmospheric pressure and 10 $kg/cm^2G$. In addition, the residence time in the coupling reaction zone is preferably between 0.1 to 10 seconds.

The catalyst which is separated in the catalyst separation step is preferably cooled before being introduced to the catalyst feedback step.

Between the catalyst separation step and the catalyst feedback step, a cracking step is preferably provided in which the separated catalyst is brought into contact with a cracking feed gas which contains a saturated hydrocarbon of $C_{2+}$, and then a cracking reaction is allowed to occur so as to produce a cracking product gas which contains an unsaturated hydrocarbon. In the cracking step, it is preferable that the catalyst is allowed to descend from the upstream so as to form a fluidized bed with the cracking feed gas.

Since the catalyst which is separated from the coupling product gas is at a high temperature, the cracking reaction, which is endothermic, proceeds by bringing the catalyst into contact with the cracking feed gas without necessity of additional heat.

The coupling method of the present invention may further comprise: a mixing step for mixing the coupling product gas and the cracking product gas so as to form a product gas mixture; a hydrocarbon separation step for separating and collecting a $C_{2+}$ hydrocarbon from the product gas mixture leaving a residual gas, which is split into a bypass gas and a branch gas; a decarbonation step for removing carbon dioxide from the branch gas leaving a decarbonated gas, which is brought into confluence with the bypass gas so as to form a confluence gas; and a methanation step for methanating the confluence gas so as to produce a methanated gas; and at least a part of the methanated gas is fed back to the coupling step as at least a part of the coupling feed gas.

By splitting the residual gas, which remains after the separation-collection of the $C_{2+}$ hydrocarbon from the coupling product gas, into the branch gas and the bypass gas, then removing carbon dioxide only from the branch gas, then methanating the decarbonated gas together with the bypass gas, and then feeding back the methanated gas to the coupling step, the burden to the decarbonation step is lightened, and thus the installation scale and the energy consumption for the decarbonation step can be reduced.

Alternatively, it is possible that the residual gas is initially methanated into a methanated gas in the methanation step, and then carbon dioxide which is contained in the methanated gas is removed in the decarbonation step leaving a decarbonated gas, at least a part of which is fed back to the coupling step as at least a part of the coupling feed gas.

By methanating the residual gas which still contains excessive carbon oxides, the equilibrium of the methanation reaction shifts toward production of methane, and thus larger amounts of hydrogen and the carbon oxides are converted into methane.

Furthermore, by methanating the residual gas, without splitting, so as to produce the methanated gas, then removing carbon dioxide from the methanated gas, and then feeding back at least a part of the decarbonated gas to the coupling step, components other than methane in the coupling feed gas are reduced, and thus the yield of the $C_{2+}$ hydrocarbon in the coupling step is improved.

Between the mixing step for mixing the coupling product gas and the cracking product gas and the hydrocarbon separation step for collecting the $C_{2+}$ hydrocarbon from the product gas mixture, a polymerization step may be provided for allowing an unsaturated hydrocarbon which is contained in the product gas mixture to polymerize.

At least a part of the coupling feed gas may be introduced to the decarbonation step so as to remove acidic impurities which are contained in the coupling feed gas. In the case where natural gas is used as the coupling feed gas, it is possible that at least a part of the natural gas is introduced to the decarbonation step so as to remove acidic impurities which are contained in the natural gas, then a saturated hydrocarbon of $C_{2+}$ which is contained in the natural gas is removed therefrom, then the thus-removed saturated hydrocarbon of $C_{2+}$ is introduced as the cracking feed gas to the cracking step, and then the residual gas is introduced as the coupling feed gas to this feedback system.

The present invention also provides an apparatus for producing a coupling product gas which contains an unsaturated hydrocarbon by allowing reaction gases, which include a coupling feed gas containing methane and a gas containing oxygen, to react in the presence of a catalyst, characterized by comprising a coupling reactor in the shape of a vertical pipe, a gas-solid separator, and a catalyst feedback means, which are connected in a loop; the coupling reactor comprising a catalyst-bed formation section, which is provided at a bottom portion of the coupling reactor, for forming a conveying catalyst bed which is formed by an ascending stream which contains the catalyst, a gas introduction nozzle for supplying at least a part of at least one of the reaction gases to the conveying catalyst bed, a coupling reaction section for producing a coupling product gas by allowing methane and oxygen to react in the presence of the catalyst, and a coupling-product-gas withdrawal outlet, which is provided at a top portion of the coupling reactor, for withdrawing the coupling product gas together with the catalyst; the gas-solid separator being provided for separating the coupling product gas and the catalyst apart; and the catalyst separation means being provided for feeding back the thus-separated catalyst to the catalyst-bed formation section of the coupling reactor.

The gas introduction nozzle of the coupling reactor may be a double-tube nozzle for simultaneously introducing at least a part of the coupling feed gas and at least a part of the gas containing oxygen. It is preferable that the gas-solid separator is a cyclone. A catalyst cooling means for cooling the catalyst is preferably provided between the gas-solid separator and the catalyst feedback means. A cracking reactor is preferably provided between the gas-solid separator and the catalyst feedback means. It is preferable that the cracking reactor is provided for forming a fluidized bed from the catalyst which is separated in the gas-solid separator and from a cracking feed gas which contains a saturated hydrocarbon of $C_{2+}$, so as to bring the catalyst and the cracking feed gas into contact with each other, and allowing a cracking reaction to occur so as to produce a cracking product gas which contains an unsaturated hydrocarbon.

The present invention will be explained in detail in the following, by way of referring to the drawings.

FIG. 1 shows an embodiment of a coupling apparatus 60 to be used for the coupling method, in which the coupling step and the cracking step are combined, according to the present invention. In FIG. 1, the coupling apparatus 60 is constructed mainly from a loop in which a coupling reactor 10, a gas-solid-separator 20, a cracking reactor 30, and a catalyst feed back means 50 are connected; and a catalyst cooling means 40.

The coupling reactor 10 is in the shape of a vertical pipe, which comprises a catalyst-bed formation section 11, which is provided at a bottom portion of the coupling reactor 10, for forming a conveying catalyst bed which is formed by an ascending stream which contains the catalyst, a gas introduction nozzle 12 for supplying a coupling feed gas containing methane and/or a gas containing oxygen to the conveying catalyst bed, a coupling reaction section 13 for producing a coupling product gas by allowing methane and oxygen to react in the presence of the catalyst, and a coupling-product-gas withdrawal outlet 14, which is provided at a top portion of the coupling reactor 10, for withdrawing the coupling product gas together with the catalyst.

The construction of the catalyst-bed formation section 11 allows a catalyst-bed formation gas 1 to be injected thereinto via a lower end 15 at a high speed so as to form the ascending stream, a catalyst 5 to be supplied from the catalyst feedback means 50 to an upper end 16 thereof so as to be mixed with the ascending stream, and the mixture to be carried upwards.

In this embodiment, the gas-solid separator 20 may be a cyclone, in which the catalyst 5 is separated from a coupling product gas 3. The catalyst 5 descends gravitationally from the cyclone 20 through a cyclone dip leg 21, lower end of which is dipped within the fluidized be of catalyst in the cracking reactor 30 to a suitable depth.

The cracking reactor 30 is a chamber in the shape of a vertical column which comprises a product-gas-mixture withdrawal outlet 31, which is provided at a top portion, a ring-shaped distributor 32, which is provided in the vicinity of a bottom portion, for introducing a cracking feed gas, and a catalyst withdrawal outlet 33, which is provided at a bottom portion. In addition, the cracking reactor 30 is provided with a cooling means 40 comprising a coiled cooling pipe above the distributor 32, or such a means as an exterior cooler to which some of the catalyst is introduced to be cooled and from which the cooled catalyst is returned to the reactor.

The catalyst which is withdrawn from a bottom portion of the cracking reactor 30 is carried from the catalyst withdrawal outlet 33 via the catalyst feedback means 50, and fed back to the catalyst-bed formation section 11 of the coupling reactor 10.

A coupling process can be carried out, for example, by using the coupling apparatus 60 in FIG. 1.

First, a coupling feed gas 1 containing methane is injected from the lower end 15 into the coupling reactor 10 so as to form therein an ascending stream of the coupling feed gas 1. By introducing a catalyst 5 from an upper end 16 of the catalyst-bed formation section 11, the catalyst 5 is mixed and dispersed in the ascending stream and carried upwards. Then, by introducing a gas containing oxygen 2 from the gas introduction nozzle 12, the coupling reaction occurs in the presence of the catalyst in the coupling reaction section 13 of the coupling reactor 10, so as to produce a coupling product gas 3 which contains a unsaturated hydrocarbon. The thus-produced coupling product gas 3, accompanied by the catalyst 5, flows out from the coupling-product-gas withdrawal outlet 14, and then is introduced into the cyclone 20.

In the cyclone, the gas and the solid, i.e., the coupling product gas 3 and the catalyst 5, are separated. The coupling product gas 3 is mixed with a cracking product gas 6 (which will be explained below) from the cracking reactor 30, and then the mixture is collected as a product gas mixture 7.

The catalyst 5 descends gravitationally from the cyclone dip leg 21, and then is suspended in the cracking reactor 30 by a cracking feed gas 8 containing a saturated hydrocarbon of $C_{2+}$, which is injected in the cracking reactor 30 via the ring-shaped distributor 32. As the catalyst 5 is fluidized in the cracking reactor 30, it makes close contact with the cracking feed gas 8.

Then, a cracking reaction occurs so as to produce a cracking product gas 6 which contains an unsaturated hydrocarbon. After the cracking product gas 6 is separated from the suspended catalyst by, for example, a secondary cyclone (which is not shown), the cracking product gas 6 is mixed with the coupling product gas 3, and then the mixture is collected as the product gas mixture 7.

In the meantime, the separated suspended catalyst is allowed to return to the cracking reactor 30.

The catalyst which is fluidized in the cracking reactor 30 is cooled by the cracking reaction which is endothermic. The catalyst is furthermore cooled to a desirable temperature by having contact with the catalyst cooling means 40. Then, the catalyst is withdrawn from a bottom portion of the cracking reactor 30, then carried from the catalyst withdrawal outlet 33 by the catalyst feedback means 50, and then fed back to the catalyst-bed formation section 11 of the coupling reactor 10 as a coupling catalyst for a following cycle.

According to the above method, since in the coupling reactor 10, the catalyst is dispersed and suspended in the ascending stream which is formed by the coupling feed gas 1, a uniform conveying catalyst bed can be formed. By introducing the gas containing oxygen 2 into the conveying catalyst bed, a coupling reaction occurs. Although the coupling reaction is exothermic, the continuous supply of coupling feed gas 1 and the catalyst 5, which have relatively low temperatures, to the coupling reaction section 13, and the continuous introduction of a regulated amount of the gas containing oxygen 2 from the gas introduction nozzle 12, as well as the immediate discharge of the coupling product gas 3 and the catalyst 5, which have reached high temperatures, to the outside of the reaction system, and the feedback of the separated catalyst 5 which has been cooled, maintains the temperature in the coupling reactor 10 within a permissible range without abrupt increases, and thus hinders the undesirable combustion reaction, improving the selectivity of the coupling reaction.

Although the coupling feed gas 1 is a gas used for forming the ascending stream according to the above embodiment, the method of the present invention is not limited to such an embodiment; for example, an inert gas such as nitrogen, or the gas containing oxygen 2 may be employed as the gas for forming the ascending stream. There may be a case in which an inert gas is advantageously used for controlling the temperature in the coupling reactor 10.

Moreover, although the entire amount of the coupling feed gas 1 is supplied to the catalyst-bed formation section 11, and the entire amount of the gas containing oxygen 2 is introduced from the sole gas introduction nozzle 12 according to the above embodiment, the method of the present invention is not limited to such an embodiment; for example, at least a part of the coupling feed gas 1 and at least a part of the gas containing oxygen 2 may be supplied from another nozzle (which is not shown) which is provided at the coupling reaction section 13, or at least a part of both gasses may be simultaneously supplied from a sole gas introduction nozzle 12. In particular, a double-tube nozzle (which is not shown) for introducing simultaneously at least a part of the coupling feed gas 1 and at least a part of the gas containing oxygen 2 may be advantageously used for controlling the temperature.

By bringing the catalyst, which is heated to a high temperature, and which is separated by the gas-solid separator (cyclone) 20, into contact with the cracking feed gas 8 in the cracking reactor 30, the cracking product gas 6 which contains an unsaturated hydrocarbon is produced. Although the cracking reaction is endothermic, the heat which is possessed by the catalyst 5 can be used for the reaction; therefore, the reaction proceeds without necessity of additional heat from outside, while the catalyst is cooled to a desirable temperature, and is fed back to the coupling reactor 10.

Since the cracking reaction is a reaction to produce an unsaturated hydrocarbon from a saturated hydrocarbon of $C_{2+}$, the concentration of the unsaturated hydrocarbon in the product gas mixture 7 increases by this reaction. That is to say, by separating in advance the natural gas into the coupling feed gas 1, which is rich in methane, and the cracking feed gas 8, which is rich in the saturated hydrocarbon of $C_{2+}$, and supplying these gases to the respective reaction systems, the yield of the unsaturated hydrocarbon as a whole which is produced from the natural gas is improved.

As the coupling feed gas 1, natural gas, or a methane-rich gas which is obtained by separating a gas which is rich in a saturated hydrocarbon of $C_{2+}$ from natural gas as in the above, may be advantageously used. However, it goes without saying that a methane-rich gas which is obtainable from another supply source can be also used.

As the gas containing oxygen 2, air can be used; however, in view of the reduction in the scale of the installation, the control of the temperature, the prevention of the formation of nitrogen oxides, and the removal of nitrogen, a gas in which nitrogen and other inert components have been removed as much as possible is preferable.

As the catalyst 5, a basic oxide having at least one element selected from the group consisting of alkaline metals, alkaline earth metals, and rare earth elements, a carbonate salt having at least one of these elements, or a compound oxide of at least two of these elements or of at least one of these elements in combination with the other elements. As examples of the catalyst 5, $SrO.La_2O_3$, $BaO.La_2O_3$, $BaO.CeO_2$, $NaMnO_4.MgO$, $Na_2P_2O_7.Mn.SiO_2$, $Li.Mn.B.MgO$, and $CaCO_3$ can be cited. These are used in the forms of powder or granule so as to be distributed and suspended in the ascending stream in the coupling reactor 10 and in the gas stream in the cracking reactor 30.

The catalyst 5 can be repeatedly used by separating it from the coupling product gas 3, then cooling it to about 750° C., and then feeding it back to the catalyst-bed formation section in the, coupling reactor 10.

As explained in the above, an extremely large amount of heat is generated in the coupling reactor 10. Especially in the vicinity of the gas introduction nozzle 12 for introducing the gas containing oxygen 2, the high concentration of the oxygen abruptly raises the temperature. In order to prevent this local overheating, the gas containing oxygen 2 may be separately supplied, as explained in the above, through at least two locations which are distant along the direction in which the gas stream ascends. This is enabled by providing gas introduction nozzles for introducing the gas containing oxygen at two locations (not shown) or more along the longitudinal direction of the coupling reactor 10. More precise control at a uniform temperature in the coupling reactor becomes possible by making the amount of the gas containing oxygen which is introduced through each gas introduction nozzle individually adjustable.

Alternatively, in order to prevent the local temperature from rising abruptly in the coupling reactor 10, at least a part of the coupling feed gas 1 may be supplied to at least one location in the ascending stream. This can be implemented by providing one or more locations on the coupling reaction section 13 with gas introduction nozzles (not shown) for introducing the coupling feed gas. In particular, by coaxially supplying the coupling feed gas and the gas containing oxygen using a double-tube nozzle, a gas in the zone where the temperature becomes highest can be diffused by a cold gas stream; therefore, this is effective in making the temperature distribution in the coupling reaction section 13 uniform. It is also possible and effective to provide a plurality of gas introduction nozzles, that is, gas introduction nozzles for introducing the gas containing oxygen and gas introduction nozzles for introducing the coupling feed gas.

In each case where these methods and apparatuses are employed, it is preferable, in order to disperse the catalyst, that at least a part of the coupling feed gas is introduced at the bottom of the coupling reactor 10.

A suitable ratio of the coupling feed gas and the gas containing oxygen which are supplied to the coupling step depends on the amount of the methane and oxygen contained respectively. It is preferable that the molar ratio of oxygen/methane is adjusted in the range between 0.05 and 0.5.

The reaction for producing ethylene by coupling proceeds basically in accordance with the following formula (2):

$$2CH_4 + O_2 \rightarrow C_2H_4 + 2H_2O \tag{2}$$

In addition, in parallel with the above reaction, ethane is produced in accordance with the following formula (3):

$$2CH_4 + \tfrac{1}{2}O_2 \rightarrow C_2H_6 + H_2O \tag{3}$$

The above reactions proceed at high selectivities when the temperature in the coupling reaction section 13 is in the range between approximately 750° C. and 900° C. On the other hand, in this temperature range, in parallel with these reactions, a combustion reaction of the coupling feed gas containing methane also occurs. When the amount of oxygen which is supplied under the above condition is less than 0.05 times that of the methane, the oxygen is in short supply; the conversion of methane decreases, and thus the yields of ethylene and ethane lower. Moreover, since the yield per pass lowers, the scale of the installation becomes too large. On the other hand, when the amount of oxygen exceeds 0.5 times that of the methane, the excessive oxygen allows the combustion to become the major reaction, and thus the selectivities of the reactions of formulae (2) and (3) for producing ethylene and methane decline.

It is preferable that the amount of the catalyst which is used in the coupling step is adjusted so that the concentration of the catalyst which is dispersed in the coupling reaction section 13 is maintained in the range between 0.5% to 5% by volume. As well as the catalyst catalytically promoting the reactions of the above formulae (2) and (3), it fulfills a role in a temperature regulating effect in which the temperature in the coupling reaction section 13 is maintained in a suitable range for the reaction. When the concentration of the catalyst is less than 0.5% by volume, the catalyst effect and the temperature regulating effect are insufficient. On the other hand, when the concentration of the catalyst exceeds 5% by weight, it becomes difficult to keep the catalyst dispersed and suspended in a stable condition. In view of the above, it is more preferable that the concentration of the catalyst is adjusted in the range between 1% and 3% by volume.

It is desirable, for the purpose of maintaining a high selectivity and a high conversion, that the temperature in the coupling reaction section 13 is adjusted to be constant in the range between 750° C. and 900° C. In particular, the reaction proceeds most smoothly at a temperature between 800° C. and 900° C. Maintenance of the temperature can be carried out by regulating the flow rates of the coupling feed gas 1 and the gas containing oxygen 2 as well as the amount of the circulating catalyst and the concentration of the catalyst; the maintenance of the temperature also depends on the temperature of the catalyst at the time of introduction. It is preferable that the catalyst to be supplied to the coupling reaction section 13 be cooled to approximately 750° C.

It is preferable that the reaction pressure in the coupling step be maintained in a range between atmospheric pressure and 10 kg/cm²G. When the reaction pressure is less than atmospheric pressure, a specific apparatus is required for decompression, and no special advantage can be obtained. When the reaction pressure exceeds 10 kg/cm²G, the combustion reaction becomes dominant, and the selectivities of the reactions for producing ethylene and methane decrease.

Since the catalyst from the coupling reactor 10 is at a high temperature, it is preferable to make an effective use of this heat. In view of this, in the cracking reactor 30, cracking of a saturated hydrocarbon of $C_{2+}$ is carried out using this catalyst at a high temperature as a heat transfer medium.

As in the above, as the cracking feed gas 8, a gas which is rich in a hydrocarbon of $C_{2+}$ which is separated from natural gas is preferably used. Among such gases which are rich in a hydrocarbon of $C_{2+}$, for example, LPG is known, which mainly contains methane, ethane, propane, butane, and the like. However, a gas rich in a hydrocarbon of $C_{2+}$ which is obtained from another source can be also used, if necessary, as a part or an entirety of the cracking feed gas 8.

The reaction for producing ethylene by cracking ethane proceeds in accordance with the following formula (4):

$$C_2H_6 \rightarrow C_2H_4 + H_2 \tag{4}$$

The above reaction is endothermic, and it proceeds by bringing the cracking feed gas 8 into contact with the catalyst which is heated to approximately 850° C. Since this reaction deprives the catalyst of heat, the temperature of the catalyst normally falls by a decrement of approximately between 50° C. and 100° C.

The cracking reactor 30 is a fluidized-bed reactor, into which the cracking feed gas 8 is introduced, for example, via a ring-shaped distributor 32 which is provided in the vicinity of a bottom portion. The catalyst 5, which is at a high temperature, is continuously supplied to the cracking reactor 30, where the catalyst 5 and the cracking feed gas 8 are brought into contact in a fluidizing state. When the temperature of the catalyst which is withdrawn from the bottom of the cracking reactor 30 is higher than approximately 750° C., the catalyst is cooled to a predetermined temperature by using the catalyst cooling means 40 as the need arises.

Since the cracking product gas 6 which is obtained as the result of the cracking contains an unsaturated hydrocarbon in a relatively high concentration, the cracking product gas 6 is mixed with the coupling product gas 3, so as to be collected as the product gas mixture 7, which is rich in the unsaturated hydrocarbon.

The thus-collected product gas mixture 7 contains reaction products such as ethylene, ethane, saturated and unsaturated hydrocarbons of $C_{3+}$, $H_2O$, and $H_2$, as well as unreacted methane and other hydrocarbons from the feeds, and CO and $CO_2$ concurrently produced as the result of the combustion reaction. It is as a matter of course that one of the purposes of the present invention is to produce the product gas mixture 7 which is rich in the $C_{2+}$ hydrocarbons; in addition, in order to enhance the total yield of the $C_{2+}$ hydrocarbons, it is desired that as much residual gas as possible remaining after collecting the product gas mixture is fed back and reused as a portion of the coupling feed gas 1.

Figure 2:
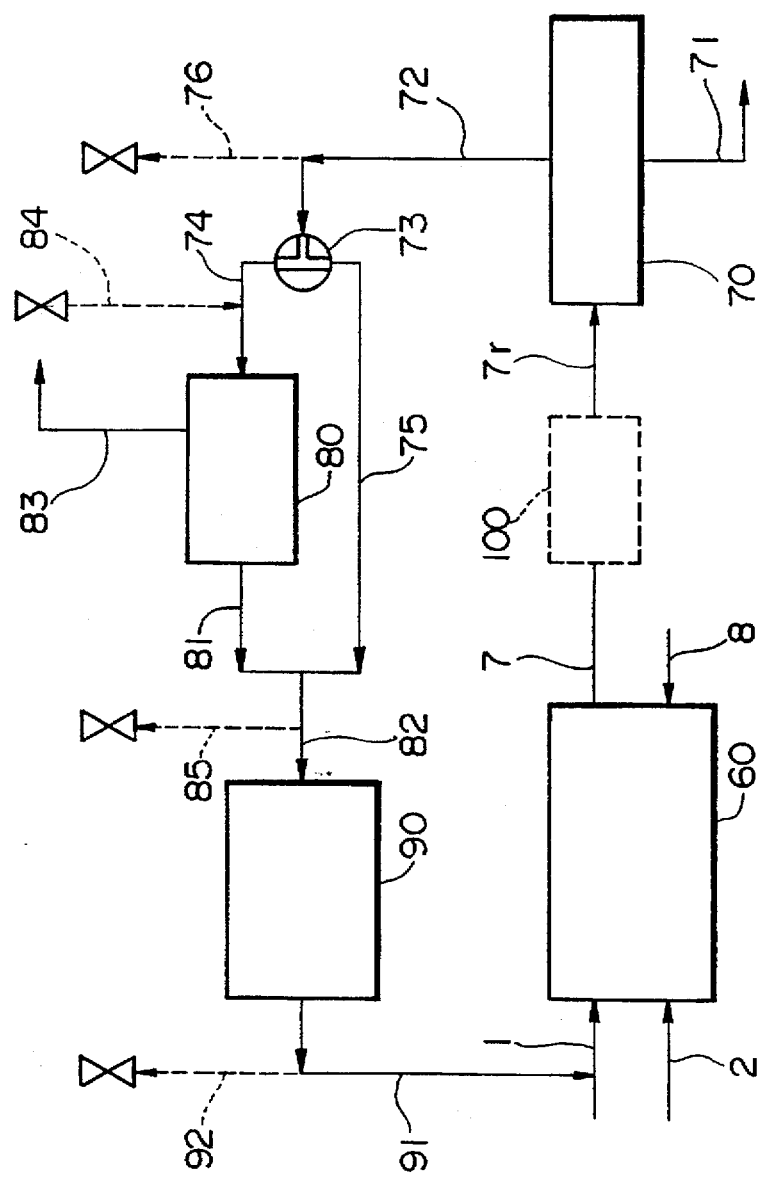
FIG. 2 is a flow diagram of an embodiment of the coupling method according to the present invention.

An embodiment of a method for reusing the residual gas is shown in FIG. 2. In FIG. 2, a product gas mixture 7 which is collected from a coupling apparatus 60 is sent to a $C_{2+}$ separation-collection apparatus 70, where a $C_{2+}$ hydrocarbon 71 is separated and collected, and the residual gas 72 mainly containing unreacted $CH_4$, $H_2$, CO, $CO_2$, and $N_2$ is sent to the feedback system.

Before the product gas mixture 7 which is withdrawn from the coupling apparatus 60 is sent to the $C_{2+}$ separation-collection apparatus 70, it may be introduced into a polymerization apparatus 100 for polymerizing an unsaturated hydrocarbon in the product gas mixture. Then, a polymerization product gas 7r is sent to the $C_{2+}$ separation-collection apparatus 70. Contents produced as the result of the polymerization in the polymerization apparatus 100 are collected from a line of the $C_{2+}$ hydrocarbon 71 as gasoline and kerosene fractions.

A feedback system to which the residual gas 72 is sent is constructed mainly from a decarbonation apparatus 80 and a methanation apparatus 90.

The residual gas 72 is split into a branch gas 74 and a bypass gas 75 by a distributing valve 73. The branch gas 74 is introduced into the decarbonation apparatus 80 in which $CO_2$ contained in the branch gas 74 is removed. A decarbonated gas 81 which is obtained after the removal of $CO_2$ is brought into confluence with the bypass gas 75. The thus-obtained confluence gas 82 is introduced into the methanation apparatus 90 so as to be methanated. At least a part of the thus-obtained methanated gas 91 is fed back to the coupling apparatus 60 as at least a part of a coupling feed gas 1.

By removing $CO_2$ from a part of the residual gas 72 according to the above method, the molar ratios of carbon oxides, consisting of CO and $CO_2$, and $H_2$, which are in the residual gas 72, are adjusted to stoichiometric ratios which are suitable for the methanation reaction. Accordingly, the obtained methanated gas 91 does not contain CO and $CO_2$ which are unnecessary for the coupling reaction, and thus the methanated gas 91 can be fed back and used as the coupling feed gas 1 which is rich in methane. Moreover, since only the branch gas 74 is decarbonated instead of the entire residual gas, the decarbonation apparatus can be small, and which consumes little energy for the decarbonation.

Molar ratios of CO, $CO_2$, and $H_2$ in the coupling product gas which is obtained from the coupling apparatus 60 according to the above embodiment is approximately as follows:

CO: 0.3~0.6% by mole $CO_2$: 1.5~3.0% by mole $H_2$: 2.0~6.0% by mole

In addition, the methanation reaction proceeds in accordance with the following formulae (5) and (6):

$$CO+3H_2 \rightarrow CH_4+H_2O \qquad (5)$$

$$CO_2+3H_2 \rightarrow CH_4+2H_2O \qquad (6)$$

Therefore, when the methanation is conducted using CO, $CO_2$, and $H_2$ in the coupling product gas without adjusting compositions, carbon oxides (CO and $CO_2$) are excessive with respect to $H_2$. When this is the case, the entire amount of $H_2$ is not consumed in the reaction with CO alone; therefore, by removing a part of $CO_2$ from the residual gas 72, the molar ratios of carbon oxides and $H_2$ can be adjusted to stoichiometric ratios which are suitable for the methanation reaction.

The splitting ratios of the branch gas 74 and the bypass gas 75 split from the residual gas 72 can be controlled by measuring the molar contents of each of the above components in the residual gas 72 and the confluence gas 82, and then adjusting distribution proportions with the distributing valve 73 so as to maintain the component ratios in the confluence gas 82 within a range of values which are most suitable for the methanation.

Figure 3:
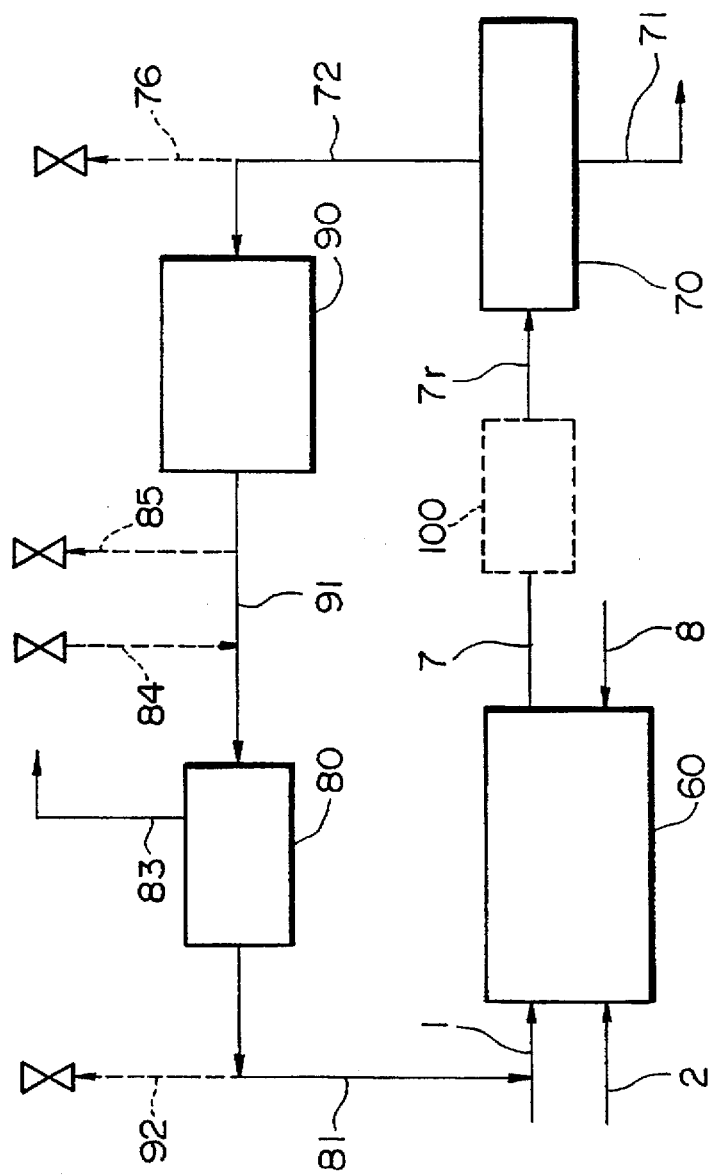
FIG. 3 is a flow diagram of another embodiment of the coupling method according to the present invention.

Another embodiment of a method for feeding back and reusing the residual gas is shown in FIG. 3. In FIG. 3, a residual gas 72, which is withdrawn from a $C_{2+}$ separation-collection apparatus 70, is sent firstly to a methanation apparatus 90, and secondly to a feedback system comprising a decarbonation apparatus 80.

When the above is the case, the residual gas 72 is first introduced into the methanation apparatus 90 so as to be methanated. The thus-obtained methanated gas 91 contains an excessive amount of $CO_2$ in addition to produced methane. Therefore, the methanated gas 91 is then introduced in the decarbonation apparatus 80, in which the surplus $CO_2$ is removed. At least a part of the thus-obtained decarbonated gas 81 is fed back as at least a part of a coupling feed gas 1 to a coupling apparatus 60.

According to the above method, since the surplus $CO_2$ is not preliminary removed from the residual gas 72, the methanation is carried out under a condition in which the amount of $CO_2$ is in excess. When the amount of $CO_2$ is in excess in the reaction of $CO_2$ and $H_2$ as expressed in the formula (6), the equilibrium of the reaction inclines toward the production of methane, and thus the amount of the unreacted residual hydrogen decreases. If the residual hydrogen is fed back to the coupling apparatus 60, oxidation of the residual hydrogen occurs in the coupling reactor 10, which tends to cause unusual temperature rising.

Therefore, the method according to the above embodiment, in which the amount of the residual hydrogen is reduced, is advantageous in controlling the temperature in the coupling reactor 10. Moreover, since acidic impurities which are produced as by-products in the methanation apparatus are removed by the decarbonation apparatus 80 which carries out the following process, the method according to the above embodiment is also advantageous in view of enhancement of the partial pressure of methane by way of removing as much surplus content as possible from the coupling feed gas.

In each embodiment of the above feedback systems, the decarbonation step carried out in the decarbonation apparatus 80 may usually employs a method in which an acidic gas is absorbed in an alkaline absorbent, and then, by heat stripping, the acidic gas is stripped from the liquid which has absorbed the acidic gas. In this method, the separated $CO_2$ is collected via a line 83. On the other hand, in the methanation apparatus 90, a gas phase reaction using a methanation catalyst is employed usually.

Natural gas sometimes contain $CO_2$ or $H_2S$, which are acidic, and in particular, $H_2S$ adversely affects the reaction and the product; therefore, when applying the method of the present invention to oxidative coupling of natural gas in such a case, $CO_2$ and $H_2S$ must be removed before the natural gas is introduced into the coupling apparatus 60. The removal can be carried out using an exclusive installation; however, by introducing natural gas via a line 84 into the decarbonation apparatus 80 as shown in FIGS. 2 and 3, the decarbonation apparatus removes $H_2S$ as well as $CO_2$, and thus the coupling feed gas 1 can be free of sulfur.

Figure 4:
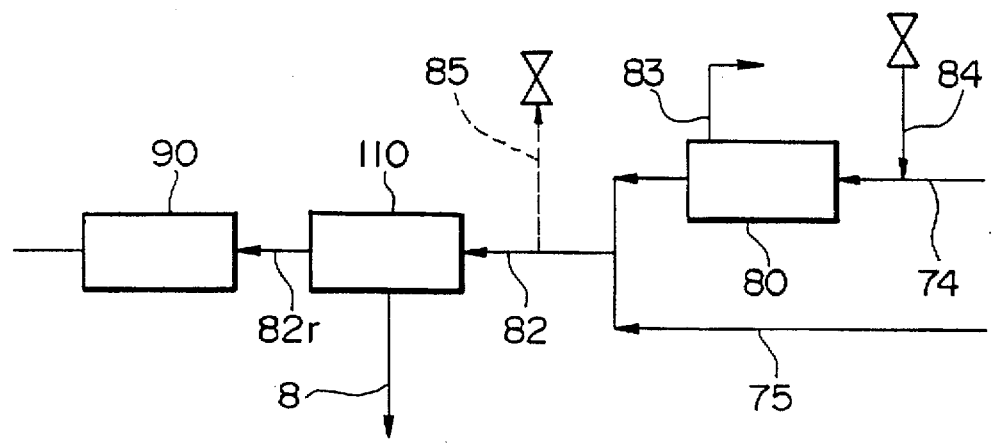
FIG. 4 is a partial flow diagram of an embodiment of the coupling method according to the present invention in which an LNG separation process is incorporated in the process shown in FIG. 2.
Figure 5:
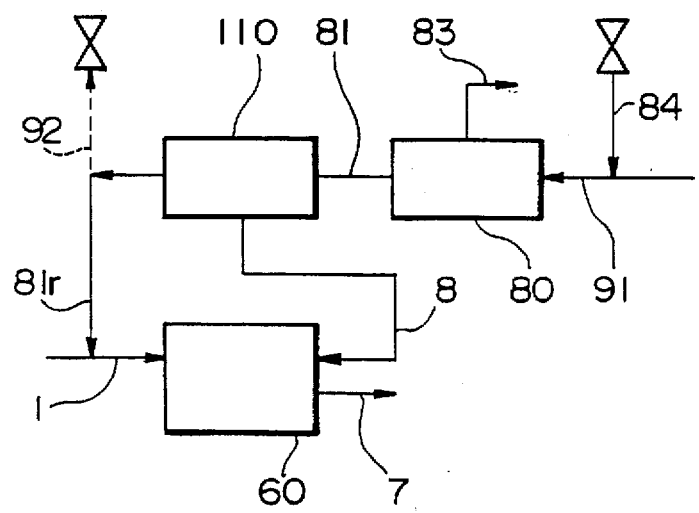
FIG. 5 is a partial flow diagram of an embodiment of the coupling method according to the present invention in which an LNG separation process is incorporated in the process shown in FIG. 3.

Moreover, as shown in FIGS. 4 and 5, it is possible that the sulfur-free natural gas can be introduced into an LNG separation apparatus 110, which is provided in a feedback system, in which a $C_{2+}$ hydrocarbon contained in the natural gas is separated out, and then the separated $C_{2+}$ hydrocarbon is supplied to a cracking reactor 30 in a cracking apparatus 60 as a cracking feed gas 8, while the remaining gas (a line 82r in FIG. 4, or a line 81r in FIG. 5) is introduced into the feed back system as a coupling feed gas. In short, FIG. 4 illustrates an embodiment of an arrangement of the LNG separation apparatus 110 in the case where the decarbonation step conducted in the decarbonation apparatus 80 as shown in FIG. 2 precedes the methanation step conducted in the methanation apparatus 90, wherein LNG separation apparatus 110 is arranged in the line of confluence gas 82. On the other hand, FIG. 5 illustrates another embodiment of an arrangement of the LNG separation apparatus 110 in the case where the methanation step conducted in the methanation apparatus 90 as shown in FIG. 3 precedes the decarbonation step conducted in the decarbonation apparatus 80. When the latter is the case, the LNG separation apparatus 110 is inserted into a decarbonated gas line 81 between the decarbonation apparatus 80 and coupling apparatus 60.

Although there may be cases where natural gas contains some or no acidic gas depending on the place of the production, the above method in any case can effect acquisition of both the coupling feed gas 1 to be supplied to the coupling apparatus 60 and the cracking feed gas 8, from the gas line.

In the feedback system of the residual gas as shown in FIGS. 2 and 3, the continuous feedback of the gas results in the gradual accumulation of gases which do not participate in the reaction, such as $N_2$. In order to remove such gases, it is preferable, with respect to the embodiments shown in FIGS. 2 and 3, that at least a part of the gas in the feedback system be continuously or intermittently purged via at least one of a purge line 76 branching from the residual gas 72, a purge line 85 branching from an intermediate portion between the decarbonation apparatus 80 and the methanation apparatus 90, and a purge line 92 branching from an input line for the coupling apparatus 60.

The coupling product gas 3, the product gas mixture 7, or the $C_{2+}$ hydrocarbon 71, which are components obtained according to the method of the present invention as explained in detail in the above, can be used as: a fuel, after each of these components are separated, or as a mixture; a material for synthesizing gasoline or kerosene fractions after the components are polymerized; or a material for other various organic syntheses. The thus-obtained products from the $C_{2+}$ hydrocarbon can be easily liquefied, and thus are convenient for storage and transportation.

EXAMPLES

Example 1

An experiment simulating a plant which can process natural gas 500000 $Nm^3$/day was carried out by using the coupling apparatus 60 as shown in FIG. 1. As for feeds, separation of a $C_{2+}$ hydrocarbon from natural gas was conducted; a fraction which was rich in methane was used as a coupling feed gas 1, while a fraction which was rich in the $C_{2+}$ hydrocarbon was used as a cracking feed gas 8. As a catalyst, $CaO$—$La_2O_3$—$LiO$—$SiO_2$ catalyst was used.

With regard to each of the coupling feed gas 1 (Line 1), the gas containing oxygen 2 (Line 2), the cracking feed gas 8 (Line 8), and the product gas mixture 7 (Line 7), the amount of each component in the unit of % by mole, the flow rate in $Nm^3$/day, the temperature in °C., and the pressure in $kg/cm^2G$ are shown in Table 1.

TABLE 1

| Line | 1 Coupling feed gas | 2 Gas containing oxygen | 8 Cracking feed gas | 7 Product gas mixture |
|---|---|---|---|---|
| $H_2O$ | 2.14 | 0.00 | 0.01 | 13.55 |
| $CO_2$ | 0.14 | 0.00 | 4.31 | 2.24 |
| CO | 0.00 | 0.00 | 0.09 | 0.48 |
| $H_2$ | 0.59 | 0.00 | 0.12 | 4.30 |
| $N_2$ | 12.38 | 0.50 | 0.91 | 9.69 |
| $O_2$ | 0.00 | 99.50 | 0.00 | 0.00 |
| $C_1$ | 84.12 | 0.00 | 58.62 | 59.71 |
| $C_2$= | 0.16 | 0.00 | 1.81 | 6.80 |
| $C_2$ | 0.46 | 0.00 | 20.13 | 1.93 |
| $C_3$= | 0.00 | 0.00 | 0.41 | 0.59 |
| $C_3$ | 0.01 | 0.00 | 5.60 | 0.24 |
| $C_4$= | 0.00 | 0.00 | 1.96 | 0.23 |
| $i$-$C_4$ | 0.00 | 0.00 | 2.90 | 0.11 |
| $n$-$C_4$ | 0.00 | 0.00 | 2.86 | 0.11 |
| $C_5$-$C_9$ | 0.00 | 0.00 | 0.21 | 0.01 |
| $C_{10}$ |  | 0.00 | 0.06 | 0.01 |
| Flow rate ($Nm^3$/day) | 43.5 | 4.4 | 6.5 | 56.3 |
| Temperature (°C.) | 305.8 | 20.0 | 490.0 | 800.0 |
| Pressure ($kg/cm^2G$) | 4.6 | 4.6 | 4.5 | 4.2 |

The results from the experiment according to Example 1 indicate that the produced amount of ethylene in the product gas mixture 7 was more than that of carbon oxides. This is believed to have resulted from the selectivity of the coupling reaction exceeding that of the oxidation reaction, since the highest temperature in the coupling reactor 10, which was detected as the temperature of the product gas mixture 7, was adjusted to 800° C. Moreover, it can be seen that the conversion of ethylene according to this method was extremely high, as the ratio of the total mole fraction of ethylene contained in the coupling feed gas 1 and the cracking feed gas 8 to the mole fraction of ethylene contained in the product gas mixture 7 was 0.1873 (feeds):3.828 (product gas mixture), i.e., 1:20.4.

Example 2

An experiment simulating a plant which can process natural gas 500000 Nm³/day was carried out by connecting the coupling apparatus 60 in Example 1 with a $C_{2+}$ separation-collection apparatus 70, a decarbonation apparatus 80, and a methanation apparatus 90 in successive order as shown in FIG. 2 so as to form a feedback system.

Thus, the product gas mixture 7 obtained by Example 1 was separated in the $C_{2+}$ separation-collection apparatus 70 into a $C_{2+}$ hydrocarbon 71 and the residual gas 72, the $C_{2+}$ hydrocarbon 71 was collected, and a part of the residual gas 72 was branched to the decarbonation apparatus 80 to be decarbonated, and the decarbonated gas 81 was brought into confluence with a bypass gas 75. From the confluence gas 82, as shown in FIG. 4, a fraction 8, which was rich in $C_{2+}$, was separated via an LNG separation apparatus 110; a fraction 82r, which was rich in methane, was methanated in the methanation apparatus 90; and the methanated gas 91 was fed back to the coupling apparatus 60. The fraction which was rich in $C_{2+}$ was used as the cracking feed gas 8.

In the meantime, the feed natural gas was introduced in the decarbonation apparatus 80 via line 84 so as to remove $H_2S$. In addition, the confluence gas 82 was purged continuously at a constant rate from a purge line 85. The distribution ratio of the branch gas 74 to the bypass gas 75 was arranged to be approximately 75:25.

The load (in kg.mol/hr) in each apparatus and line is shown in FIG. 2.

Comparative Example 1

An operation according to Example 2 was repeated except that the bypass line 75 was closed so that the entire amount of the residual gas 72 was supplied from the branch gas line 74 to the decarbonation apparatus 80, and shortage in $CO_2$ in the methanation apparatus 90 was supplied from the outside, via a line (which is not shown), to the methanation apparatus 90 according to a conventional method.

The load (in kg.mol/hr) in each apparatus and line is shown in Table 2.

TABLE 2

| Step | Line No. | Example 2 (kg.mol/hr) | Comparative Example 1 (kg.mol/hr) |
| --- | --- | --- | --- |
| Feed gas | 84 | 930.1 | 930.1 |
| Gas containing oxygen | 2 | 532.0 | 532.0 |
| Bypass gas | 75 | 1563.3 | 0.0 |
| Branch gas | 74 | 5657.7 | 7221.0 |
| Decarbonation step | 80 | 5477.3 | 7002.5 |
| Supplementary $CO_2$ | | 0.0 | 38.1 |
| Purging gas | 85 | 132.3 | 132.3 |
| Confluence gas | 82 | 6908.3 | 6908.3 |
| Methanated gas | 91 | 6160.7 | 6160.7 |

With regard to each of Example 2 and Comparative Example 1, the gas supply amount and $CO_2$ processing amount (both amounts are expressed in kg.mol/hr) in the decarbonation apparatus 80, and the thermal load (in kcal/hr) in a stripping column (not shown) for $CO_2$ stripping are shown in Table 3.

TABLE 3

| | Example 2 | Comparative Example 1 |
| --- | --- | --- |
| Amount of gas supplied (kg.mol/hr) | 5657.7 | 7221.0 |
| Amount of $CO_2$ processed (kg.mol/hr) | 180.4 | 218.5 |
| Thermal load in stripping column (kcal/hr) | $5.6 \times 10^6$ | $6.9 \times 10^6$ |

The above results indicate that, in comparison with the conventional method according to Comparative Example 1 in which the residual gas 72 was not branched, the method of Example 2, in which the residual gas 72 was branched, reduced 22% of the amount of gas supplied, 17% of the amount of $CO_2$ processed and 19% of the thermal load. However, there was no difference between Example 2 and comparative Example 1 in the loads in the methanation apparatus 90 and coupling apparatus 60.

Example 3

An experiment simulating a plant which can process natural gas 500000 Nm³/day was carried out by connecting the coupling apparatus 60 in Example 1 with a $C_{2+}$ separation-collection apparatus 70, a methanation apparatus 90, and a decarbonation apparatus 80 in successive order as shown in FIG. 3 so as to form a feedback system.

Thus, the product gas mixture 7 obtained by Example 1 was separated in the $C_{2+}$ separation-collection apparatus 70 into a $C_{2+}$ hydrocarbon 71 and the residual gas 72, the $C_{2+}$ hydrocarbon 71 was collected, and the entire amount of the residual gas 72 was initially methanated in the methanation apparatus 90, the methanated gas 91 was decarbonated in the decarbonation apparatus 80, the decarbonated gas 81 was processed in the LNG separation apparatus 110, and the fraction 81r which was rich in methane was fed back to the coupling apparatus 60.

In the meantime, the feed natural gas was introduced in the decarbonation apparatus 80 via line 84 so as to remove $H_2S$. In addition, the confluence gas 85 was purged continuously at a predetermined rate from a purge line 85.

With regard to each of Example 3 and Comparative Example 1, the $H_2$ conversion (%) and $CO_2$ consumption (kg.mol/hr) are shown in Table 4. It is noted that in Comparative Example 1, $CO_2$ in stoichiometric ratio corresponding to hydrogen in the feed gas was added to the methanation apparatus 90. In addition, in each of Example 3 and Comparative Example 1, approximately the entire amount of CO in the feed gas was methanated.

TABLE 4

| | Example 3 | Comparative Example 1 |
| --- | --- | --- |
| $H_2$ conversion (%) | 95.0 | 89.3 |
| $CO_2$ consumption (kg.mol/hr) | 32.3 | 30.5 |

The above results indicate that the equilibrium of methanation shifted toward the production of methane according to the method of Example 3 in which an excessive amount of carbon oxides were supplied to the methanation apparatus 90; thus, both the $H_2$ conversion and $CO_2$ consumption were improved in comparison with Comparative Example 1. These results indicate that amounts of $H_2$, $CO_2$, and $H_2O$, which would hinder the coupling reaction, in the feed gas 1 which was supplied to the coupling apparatus was reduced.

By comparing Example 2 with Example 3, it can be concluded that, when the method is designed to reduce the load to the decarbonation apparatus 80 and to reduce the installation scale and energy consumption thereof, the method of Example 2 should be preferably adopted; and, when the method is designed to reduce as much as possible components other than methane in the feed gas 1 to be supplied to the coupling apparatus 60 so as to improve the reaction ratio of the coupling reaction, the method of Example 3 should be preferably adopted.

What is claimed is:

1. An apparatus for oxidative coupling of methane whereby reaction gases, which include a coupling feed gas containing methane and a gas containing oxygen, are allowed to react in the presence of a catalyst, and a coupling product gas containing an unsaturated hydrocarbon is produced;

said apparatus for oxidative coupling of methane comprising a coupling reactor in a shape of a vertical pipe, a gas-solid separator, and a catalyst feedback means, which are connected in a loop;

said coupling reactor comprising a catalyst-bed formation section, which is provided at a bottom portion of said coupling reactor, for forming a conveying catalyst bed which is formed by an ascending stream which contains said catalyst, a gas introduction nozzle for supplying at least a part of at least one of said reaction gases to said conveying catalyst bed, a coupling reaction section for producing a coupling product gas by allowing methane and oxygen to react in the presence of said catalyst, and a coupling-product-gas withdrawl outlet, which is provided at a top portion of said coupling reactor, for withdrawing said coupling product gas together with said catalyst;

said gas-solid separator being provided for separating said coupling product gas and said catalyst; and said catalyst feedback means being provided for feeding back said catalyst, which is separated in said gas-solid separator, to said catalyst-bed formation section of said coupling reactor wherein said apparatus for oxidative coupling of methane further comprises between said gas-solid separator and said catalyst feedback means, a catalyst cooling means for cooling said catalyst.

2. An apparatus for oxidative coupling of methane as in claim 1, wherein said gas introduction nozzle is a double-tube nozzle for simultaneously introducing at least a part of said coupling feed gas and at least a part of said gas containing oxygen.

3. An apparatus for oxidative coupling of methane as in claim 1, wherein said gas-solid separator is a cyclone.

4. An apparatus for oxidative coupling of methane as in claim 1, wherein said apparatus for oxidative coupling of methane further comprises, between said gas-solid separator and said catalyst feedback means, a cracking reactor for forming a fluidized bed from said catalyst which is separated in said gas-solid separator and a cracking feed gas which contains a saturated hydrocarbon having a carbon number of at least 2, so as to bring said catalyst and said cracking feed gas into contact with each other, and for allowing a cracking reaction to occur so as to produce a cracking product gas which contains an unsaturated hydrocarbon.

* * * * *